United States Patent [19]

Elango

[11] Patent Number: 5,235,090

[45] Date of Patent: Aug. 10, 1993

[54] SYNTHESIS OF 2-(4'-AMINOPHENYLOXY) ALKANOIC ACIDS & ACIDS & ESTERS & THEIR DERIVATIVES

[75] Inventor: Varadaraj Elango, Corpus Christi, Tex.

[73] Assignee: Hoechst Celanese Corp., Somerville, N.J.

[21] Appl. No.: 979,399

[22] Filed: Nov. 19, 1992

Related U.S. Application Data

[60] Continuation of Ser. No. 570,479, May 28, 1991, abandoned, which is a division of Ser. No. 312,144, Feb. 17, 1989, abandoned, which is a division of Ser. No. 170,712, Mar. 21, 1988, Pat. No. 4,883,901.

[51] Int. Cl.$^5$ .................. C07C 229/40; C07C 229/42
[52] U.S. Cl. ........................... 560/45; 562/455
[58] Field of Search .................. 560/45; 562/455

[56] References Cited

U.S. PATENT DOCUMENTS 3,081,302  3/1963  Shapiro et al. ................ 560/45
3,746,741  7/1973  Hubele ............................ 560/34

OTHER PUBLICATIONS

Berti, *Chemical Abstracts*, vol. 53, No. 14106d (1959).
Winzer et al., *Chemical Abstracts*, vol 65, No. 19739a (1966).
Winzer et al., "Zur NACl-Floatation mit Phenoxy essigsäure ederivaten", Bergakademie, 18Jg Heft 8, Aug. 1966.
Suter et al., English Translation of Swiss Publication 480070 (1969).

*Primary Examiner*—José G. Dees
*Assistant Examiner*—B. Frazier
*Attorney, Agent, or Firm*—Michael W. Ferrell

[57] ABSTRACT

A method for synthesizing 2-(4-amidophenoxy)alkanoic acids and esters and 2-(4-aminophenoxy)alkanoic acids and esters by reacting a hydroxyaromatic ketone derivative with a 2-substituted alkanoic acid or ester under basic conditions and thereafter reacting with a hydroxylamine derivative and conducting a Beckmann Rearrangement with subsequent solvolysis.

6 Claims, No Drawings

SYNTHESIS OF 2-(4'-AMINOPHENYLOXY) ALKANOIC ACIDS & ACIDS & ESTERS & THEIR DERIVATIVES

This is a continuation of copending application Ser. No. 07/570,479 filed on May 28, 1991, now abandoned, which is a divisional of application Ser. No. 07/312,144 filed Feb. 17, 1989, now abandoned which is a divisional of application Ser. No. 07/170, 712, filed on Mar. 21,. 1988, now U.S. Pat. No. 4,883,901.

BACKGROUND OF THE INVENTION

The present invention relates to a method for the synthesis of 2-(4-amidophenoxy)alkanoic acids and esters and 2-(4-aminophenoxy)alkanoic acids and esters. Such compounds are useful in the production of pharmaceuticals and herbicides. See, for example, U.S. Pat. Nos. 3,278,524; 3,081,302; 4,439,226, 4,358,307 and British Patent 916,242.

U.S. Pat. No. 3,278,524, teaches the preparation of 2-(4-acetaminophenoxy)propanoic acid by reacting 2-halo propionic acids with 4-acetaminophenol under basic conditions. Similarly, U.S. Pat. No. 3,081,302, teaches the condensation of 4-acetaminophenol with 2-halo-alkanoic acid esters in the presence of a base to give 2-(4-acetaminophenoxy)alkanoic acid esters. Such a process is economically disadvantageous, and hence the poor yield.

U.S. Pat. No. 4,439,226, and Journal of Organic Chemistry (Vol.36, pages 1171–1175, 1971) describe the synthesis of 2-(4-aminophenoxy)propanoic acid esters via sequential condensation of 4-nitrophenol with 2-halopropanoic acid esters in the presence of a base and reduction. These processes proceeds with moderate yields and hence they are not economically advantageous. Furthermore, salts of nitrophenols can explode if allowed to become dry, especially if heated.

The prior art does not disclose the conversion of acylaromatic compounds to the corresponding acetamide or aminoaromatic compounds. Such a process would be economically desired as it overcomes the deficiencies mentioned heretofore.

The present invention provides a procedure for producing intermediates which are 2-(4-aminophenoxy)alkanoic acids or esters, preferably, 2-(4-acetaminophenoxy)alkanoic acids or esters as well as 2-(4-aminophenoxy)alkanoic acids or esters.

SUMMARY OF THE INVENTION

The invention provides a method for synthesizing 2-(4-amidophenoxy)alkanoic acids or esters as well as 2-(4-aminophenoxy)alkanoic acids or esters which comprises reacting a hydroxyaromatic ketone or benzaldehyde derivative of the formula

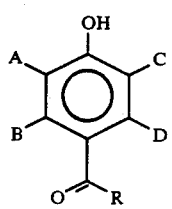

(I)

or a salt thereof; with a substituted acid or ester of the formula

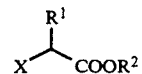

under basic conditions to thereby form a 2-4-(acylphenoxy)alkanoic acid or ester derivative (II) of the formula

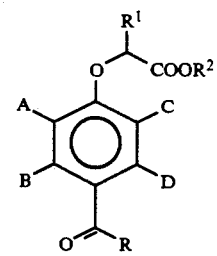

(II)

This 2-(4-acylphenoxy)alkanoic acid or ester (II) is then reacted with a hydroxylamine derivative to form a 2-(4-acyliminophenoxy) alkanoic acid or ester (III) of the formula

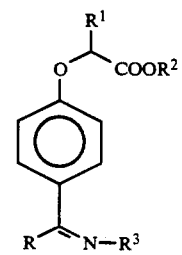

(III)

which is then subjected to a Beckmann Rearrangement to obtain a 2-(4-amidophenoxy)alkanoic acid or ester (IV) of the formula

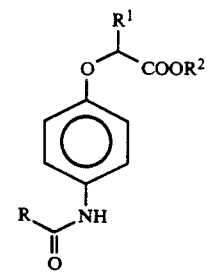

(IV)

In order to obtain 2-(4-aminophenoxy)alkanoic acids and esters, the aforesaid 2-(4-amidophenoxy)alkanoic acid or ester (V) is hydrolyzed with $R^4OH/H^+$ to obtain a compound of the formula:

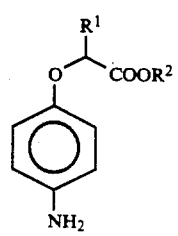

(V)

In the above formulae:

R is H, $C_1$ to $C_{18}$ alkyl or $C_6$ to $C_{18}$ aryl, preferably H, or $C_1$ to $C_4$ alkyl, most preferably H or methyl; and wherein $R^1$ is H, phenyl or $C_1$ to $C_{18}$ alkyl, preferably H, or $C_1$ to $C_4$ alkyl, and most preferably H or methyl; and where $R^2$ and $R^4$ are independently H $C_1$ to $C_{18}$ alkyl, preferably $C_1$ to $C_4$ alkyl or aryl such as phenyl or naphthyl which may be substituted or unsubstituted; $R^3$ is OH, O—$SO_3H$; and A, B, C and D are independently H, X, $CF_3$, $NO_2$, CN, $C_1$ to $C_4$ alkyl or alkoxy, or $C_6$ to $C_{10}$ aryl, protected using methods well-known to those skilled in the art so to avoid reaction of said substituents under the conditions of the process, i.e., alkylation, oximation, solvolysis; and X is F, Cl, Br, I or sulfonic ester. The compounds of the formulae II, III, IV and V possess an asymmetric carbon center and can therefore occur as pure enantiomers (optically active) or racemic as mixtures of enantiomers.

DETAILED DESCRIPTION OF THE PREFERRED EMBODIMENT

In the production of the alkanoic acids and esters of this invention, one preferably begins with a hydroxyaromatic ketone and reacts it with one of the aforesaid substituted acids or esters under basic conditions. This reaction product is then reacted with a hydroxylamine derivative and then subjected to a Beckmann rearrangement in the presence of a catalyst. The resulting product is the desired 2-(amidophenoxy)alkanoic acid or ester. This resulting product may then hydrolyzed or alcoholized to obtain the desired 2-(4-aminophenoxy)alkanoic acid or ester. The reaction sequence may be generalized as:

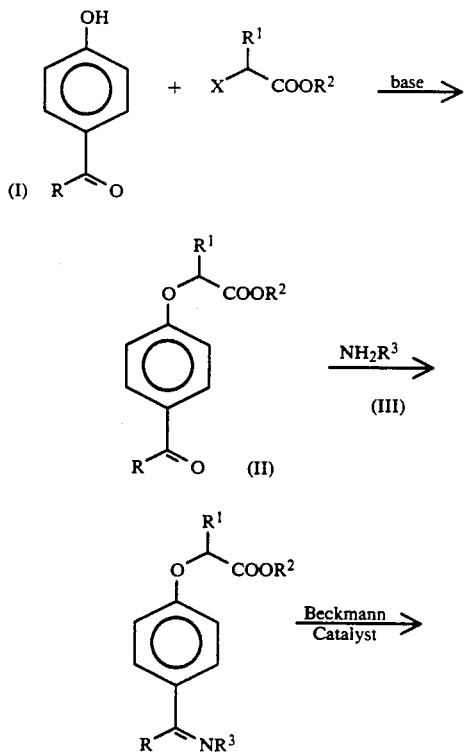

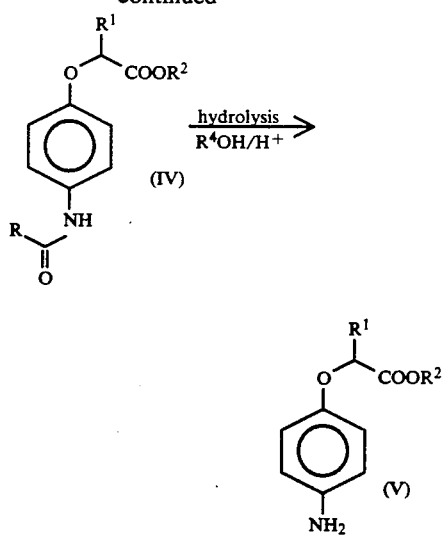

The preferred embodiment will now be set forth in further detail, and the skilled artisan can well obtain the analogous compounds. An important feature of this invention is to begin the synthesis with a hydroxyaromatic ketone (I) or benzaldehyde derivative which is preferably a 4-hydroxyacetophenone compound. The most preferred compound is 4-hydroxyacetophenone, as well as its sodium and potassium salts. The hydroxyaromatic ketone is then reacted with one of the aforesaid X-substituted acids or esters which may be optically active or racemic. Preferred esters are halogen substituted propanoates such as methyl 2-chloropropanoate, methyl 2-bromopropanoate, and ethyl 2-chloropropanoate, alkyl 2-[(methylsulfonyl)oxy]propanoate and alkyl 2-[(toluylsulfonyl)oxy]propanoate. This reaction proceeds by the Williamson's ether synthesis which is also well known to the skilled artisan. The reaction may take place by refluxing the hydroxyaromatic ketone with the ester in a solvent such as dimethylformamide under basic conditions. The basic conditions may be provided either by use of a base such as an alkali metal or alkaline earth metal hydroxide or carbonate, amines or a hydride such as sodium hydride. Alternatively, within the meaning of this invention, the basic media may be provided by using one of the aforesaid salt forms of the hydroxyaromatic ketones, such as 4-hydroxyacetophenone sodium or potassium salt. Alternative solvents for the refluxing reaction non-exclusively include polar protic solvents, e.g., water or alcohol; or polar aprotic solvents, e.g., ketones, ethers, nitriles, and sulfoxides. The reaction may take place at a temperature of from about 0.1 to about 100 hours, or more preferably from about 1 to about 50 hours at a temperature of from about 0° C. to about 200° C. or more preferably from about 25° C. to about 200° C. The reaction product of this juncture is a 2-(4-acylphenoxy)alkanoic ester derivative. In the preferred embodiment the foregoing reactants are 4-hydroxyacetophenone potassium salt and methyl 2-bromopropionate with refluxing in dimethylformamide. Therefore the preferred compound produced is methyl 2-(4-acetylphenoxy)propionate. In the alternative, instead of the aforesaid substituted ester, one could use a substituted acid of the formula:

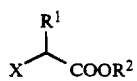

wherein $R^2$ is as described before is conducted prior to the oxidation step. This component is then reacted with an amine such as $H_2N-R^3$ wherein $R^3$ is OH, O—SO$_3$H, where R is as described before. In the most preferred embodiment, hydroxylamine is employed. Other preferred amines non-exclusively include hydrazoic acid and hydroxylamine-O-sulfuric acid. The reaction product at this point is a 2-(4-acyliminophenoxy)alkanoic acid or ester.

This component is then subjected to a Beckmann Rearrangement process which is well known to the skilled artisan per se. This causes a shift of the $R^3$ group from its carbon bond to a bond with the nitrogen. The rearrangement is conducted with any commonly employed Beckmann catalyst. In the preferred embodiment an acid catalyst is used in a suitable solvent. The most preferred acid is sulfuric acid. Others non-exclusively include thionyl chloride and polyphosphoric acid. One preferred solvent is acetic acid. Alternative solvents non-exclusively include carboxylic acids, esters, nitriles and ethers. The reaction may take place at a temperature of from about 0.1 to about 12 hours, or more preferably from about 0.5 to about 6 hours at a temperature of from about 40° C. to about 130° C. or more preferably from about 80° C. to about 120° C.

The reaction product of this juncture is a 2-(4-acetamidophenoxy)alkanoic acid or ester which in the preferred embodiment is a 2-(4-acetamidophenoxy)-propanoic acid or ester. This latter component may then be hydrolyzed or alcoholyzed. The alcoholysis may be conducted by contacting with alcohols under acidic conditions and elevated temperatures for a period of time sufficient to permit the reaction to approach completion. The amount of alcohol used may be, for example, about 0.5 to about 1,000 mol equivalents, preferably about 1 to about 100 mol equivalents based on the ester being alcoholized. The acids which may be employed for this purpose are organic acids such as methanesulfonic acid, para-toluenesulfonic acid, mineral acids such as sulfuric, hydrochloric and phosphoric acids, and acidic ion exchange resins. In some instances, it may be desirable to employ a combination of alcohol and water to achieve a measure of solvolysis. The hydrolysis may be conducted by refluxing with alcohols, ion exchange resins and/or acids such as hydrochloric acid and sulfuric acid.

Hydrolysis may take place at from about 0.1 to about 10 hours, or more preferably from about 0.5 to about 4 hours at a temperature of from about 20° C. to about 200° C., or more preferably from about 60° C. to about 140° C. The reaction is conducted with an anticipated conversion of from about 90% to about 99% with a selectivity of from about 90% to about 98%. The solvolysis product is a 2-(4-aminophenoxy)alkanoic acid or ester which in the preferred embodiment is a 2-(4-aminophenoxy)propanoic acid or ester. The alcoholysis process of this invention provides for the recovery of the amino product in relatively higher yields. The product may be recovered by conventional purification methods usually involving a combination of crystallization, filtration, washing and distillation in any order deemed advantageous for the system at hand.

The following non-limiting examples serve to illustrate the invention.

EXAMPLE 1

To a solution of 4-hydroxyacetophenone potassium salt (8.8 g, 500 mmol) in methanol (50 mL) is added methyl 2-bromopropanoate (11.08, 65.0 mmol) dropwise over 30 minutes under nitrogen. The mixture is refluxed under nitrogen for 24 hours during which KBr is accumulated. The reaction is monitored by thin layer chromatography using 100% ethyl acetate. The reaction is cooled to room temperature and the KBr is filtered out. Ethyl acetate (50 ml) is added to give a turbid solution which is refiltered. The reaction product is analyzed by GLC and found to yield methyl 2-(4-acetylphenoxy)propanoate (13.2 g). (m.p. 54.8 ° C.); IR (KBr) 1757.7 (vs), 1666.8 (vs); $^1$H NMR (CDCl$_3$) delta 1.54 (d, J=6.8 Hz, 3H), 2.42 (s, 3H), 3.64 (s, 3H), 4.76 (q, J=6.8 Hz, 1H), 6.79 and 7.80 (dd, J=8.0 Hz, 4H).

EXAMPLE 2

To a solution of the potassium salt of 4-hydroxyacetophenone (25.0 g, 0.14 mol) in dimethylformamide (DMF) (100 mL) is added methyl 2-chloropropanoate (24.5 g, 0.20 mol) over 30 minutes and stirred at 85°-90° C. for 3 hours under nitrogen. The reaction is filtered to remove KCl and the filtrate is concentrated under reduced pressure to remove DMF and the product analyzed by GLC. The product is dissolved in ethyl acetate (300 mL) and extracted with 2N NaOH (2×100 mL) and water (100 mL). The organic phase is dried and concentrated to give pure methyl 2-(4-acetylphenoxy)-propanoate (25 g) (yield 64%).

EXAMPLE 3

To a solution of the potassium salt of 4-hydroxyacetophenone (25.0 g, 0.14 mol) in DMF (100 mL) is added ethyl 2-chloropropanoate (27.3 g, 0.20 mol) over 30 minutes and stirred at 85°-90° C. for 3 hours under nitrogen. The reaction is filtered to remove KCl and the filtrate is concentrated under reduced pressure to remove DMF and the product is analyzed by GLC. The product is dissolved in ethyl acetate (300 mL) and extracted with 2N NaOH (2×100 mL) and water (100 mL). The organic phase is dried and concentrated to give pure ethyl 2-(4-acetylphenoxy)propanoate (30 g) (yield 75%); m.p. 49.6° C.; IR (KBr) 1747.7 (vs), 1669.8 (vs); $^1$H NMR (CDCl$_3$) delta 1.18 (t, J=7.2 Hz, 3H), 1.58 (d, J=6.8 Hz, 3H), 2.46 (s, 3H), 4.15 (q, J=7.2, 2H), 4.77 (q, J=6.8, 1H), 6.83 and 7.84 (dd, J=9.0 Hz, 4H).

EXAMPLE 4

A solution of the potassium salt of 4-hydroxyacetophenone (17.6 g, 0.1 mol) in DMF (50 mL) is added to a solution of ethyl L-2-[(methylsulfonyl)oxy]-propanoate (21.5 g, 0.11 mol) in DMF (40 mL) over 15 minutes at 80° C. and stirred at 80° C. for 2 hours. To the reaction is added ethyl acetate (100 mL) and filtered. The filtrate is concentrated under reduced pressure whereupon the product is analyzed by GLC. The product is dissolved in ethyl acetate (250 mL) and extracted with saturated sodium bicarbonate solution (2×100 mL) and water (2×60 mL). The organic phase is dried and concentrated to give ethyl D4-(4-acetylphenoxy)propanoate (20.2 g).

EXAMPLE 5

Potassium hydroxide (17.0 g, 0.3 mol) is added to water (50 mL) and allowed to dissolve. The solution is added to 4-hydroxyacetophenone (13.6 g, 0.1 mol) to produce the potassium salt of 4-hydroxyacetophenone. 2-Bromopropanoic acid (17.0 g, 0.11 mol) is added to the potassium salt of 4-hydroxyacetophenone to give a yellow suspension. The solution is heated to reflux (102° C.) during which a yellow solution results. The solution is refluxed for 24 hours and cooled to room temperature. The pH is adjusted to 6–7 and extracted with ethyl acetate (3×100 mL) and the solution is concentrated under reduced pressure. The aqueous layer is acidified to pH 2 and extracted with ethyl acetate (3×150 mL). The solution is concentrated to give 7.0 g of a brown liquid which is 2-(4-acetylphenoxy)propanoic acid at a yield of 34%.

EXAMPLE 6

To a solution of the potassium salt of 4-hydroxyacetophenone (8.8 g, 0.05 mol) in dimethylformamide (25 mL) is added methyl 2-bromopropanoate (10.2 g, 0.06 mol) over 30 minutes and stirred at 80°–90° C. for 4 hours under nitrogen. The reaction is cooled to room temperature and methylene chloride (75 mL) and water (75 mL) are added. The organic phase is separated, washed with water (100 mL), dried and concentrated to give methyl 2-(4-acetylphenoxy)propanoate (8.5 g) (yield 76%). Methyl 2-(4-acetylphenoxy)propanoate (7.0 g, 31.5 mmol) is combined with 2N NaOH (20 mL) and refluxed overnight. Water (30 mL) is added to the reaction which is then washed with methylene chloride (50 mL). It is then acidified to pH=1 with concentrated hydrochloric acid and extracted with ethyl acetate (3×100 mL). The organic phase is dried and concentrated to provide 2-(4-acetylphenoxy)propanoic acid (5.0 g) (yield 92%): m.p. 104.3° C., IR (KBr) 3000 (br, vs), 2940 (br,s), 1754 (vs), 1650 (vs); $^1$H NMR (CDCl$_3$) delta 1.69 (d, J=6.8 Hz, 3H), 2.55 (s,3H), 4.8 (q, J=6.8 Hz, 1H), 6.92 and 7.93 (dd, J=9.0 Hz, 4H).

EXAMPLE 7

A solution of 2-(4-acetylphenoxy)propionic acid (1.5 g, 7.2 mmol), hydroxylamine sulfate (0.72 g, 4.4 mmol), and concentrated sulfuric acid (2 drops) in acetic acid (30 mL) is refluxed for 4.25 hours. The reaction is quenched with sodium carbonate (0.25 g, 2.4 mmol) and concentrated to give a residue. The reaction residue is dissolved in water (50 mL) and extracted with ethyl acetate (2×100 mL). The ethyl acetate extract is dried and concentrated to give 2-(4-acetamidophenoxy)propionic acid (1.53 g) (yield 95%): m.p. 170°–172° C.; IR (KBr) 3400 (vs), 2900 (s) 1730 (vs), 1630 (vs), and 1603 (vs); $^1$H NMR (DMSO-d$_6$) delta 1.47 (d, J=6.8 Hz, 3H), 1.87 (s,3H), 2.06 (s,3H), 4.65 (q, J=6.8 Hz, 1H), 6.73 and 7.42 (dd, J=9.0 Hz, 4H).

EXAMPLE 8

To a solution of 2-(4-acetamidophenoxy)propionic acid (0.5 g, 2.2 mmol) in ethanol (10 mL) is added a drop of concentrated sulfuric acid and refluxed for 4 hours. The reaction is concentrated to dryness to give a residue. The residue is partitioned between water and ethyl acetate. The ethyl acetate layer is collected, dried (MgSO$_4$), and concentrated to give ethyl 2-(4-acetamidophenoxy)propanoate (0.44 g) (yield 80%): $^1$H NMR (CDCl$_3$) delta 1.27 (t, J=7.0 Hz, 3H), 1.60 (d, J=7.0 Hz, 3H), 4.25 (q, J=7.0 Hz, 2H), 4.76 (q, J=7.0 Hz, 1H), 6.84 and 7.46 (dd, J=9.0 Hz, 4H), and 8.02 (s, 1H).

EXAMPLE 9

Ethyl 2-(4-acetamidophenoxy)propanoate (5.0 g, 2.0 mmol) is hydrolyzed by refluxing for 6 hours at 80° C. with ethanol (10 mL) and 3 drops of concentrated hydrochloric acid. The reaction is concentrated under reduced pressure to obtain ethyl 2-(4-aminophenoxy)propanoate (0.4 g) (yield 95%).

What is claimed is:

1. A 2-(4-amidophenoxy) alkanoic acid or ester of the formula

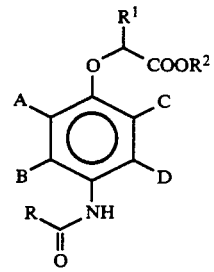

wherein at least one of A, B, C, and D are fluorine and the rest of A, B, C, and D are hydrogen and $R^1$, $R^2$, and R are independently H, $C_1$–$C_{16}$ alkyl or aryl.

2. The compound of claim 1 wherein A, B, C, and D are fluorine.

3. The compound of claim 1 wherein $R^1$ and $R^2$ are independently hydrogen, methyl or ethyl.

4. The compound of claim 1 wherein R is H or aryl.

5. The compound of claim 1 wherein R, $R^1$ and $R^2$ are methyl groups.

6. The compound of claim 1 wherein $R^1$ is H, and R and $R^2$ are $CH_3$.

* * * * *